US011813027B2

(12) United States Patent
Link et al.

(10) Patent No.: US 11,813,027 B2
(45) Date of Patent: Nov. 14, 2023

(54) SYSTEM AND METHOD FOR POSITIONING A SURGICAL TOOL

(71) Applicant: Waldemar Link GmbH & Co. KG, Hamburg (DE)

(72) Inventors: Helmut D. Link, Hamburg (DE); Riccardo Signoretti, Jersey City, NJ (US)

(73) Assignee: Waldemar Link GmbH & Co. KG, Hamburg (DE)

( * ) Notice: Subject to any disclaimer, the term of this patent is extended or adjusted under 35 U.S.C. 154(b) by 314 days.

(21) Appl. No.: 16/442,155

(22) Filed: Jun. 14, 2019

(65) Prior Publication Data

US 2019/0380789 A1    Dec. 19, 2019

Related U.S. Application Data

(60) Provisional application No. 62/763,491, filed on Jun. 15, 2018.

(51) Int. Cl.
*A61B 34/20* (2016.01)
*A61B 34/00* (2016.01)

(52) U.S. Cl.
CPC .............. *A61B 34/20* (2016.02); *A61B 34/25* (2016.02); *A61B 2034/2048* (2016.02); *A61B 2034/2065* (2016.02)

(58) Field of Classification Search
USPC ........................................................ 600/424
See application file for complete search history.

(56) References Cited

U.S. PATENT DOCUMENTS

| 8,057,482 | B2 | 11/2011 | Stone et al. | |
|---|---|---|---|---|
| 2005/0049486 | A1* | 3/2005 | Urquhart | A61B 34/20 600/429 |
| 2010/0198402 | A1* | 8/2010 | Greer | B25J 3/04 901/41 |
| 2014/0135616 | A1* | 5/2014 | Stein | A61B 17/92 600/424 |
| 2017/0165008 | A1* | 6/2017 | Finley | A61B 6/547 |
| 2017/0252110 | A1 | 9/2017 | Link et al. | |
| 2018/0012413 | A1* | 1/2018 | Jones | G06T 19/006 |
| 2019/0350657 | A1* | 11/2019 | Tolkowsky | A61B 6/5258 |

FOREIGN PATENT DOCUMENTS

WO    WO-2016030512 A1 *    3/2016    ......... A61B 17/7074

* cited by examiner

*Primary Examiner* — Jason M Ip
*Assistant Examiner* — Renee C Langhals
(74) *Attorney, Agent, or Firm* — CHIESA SHAHINIAN & GIANTOMASI PC

(57) ABSTRACT

A surgical navigation system for providing computer-aided surgery. The surgical navigation system includes a handheld surgical tool with computer-aided navigation, an imaging device, an alignment module, and a user interface module. The handheld surgical tool includes at least one sensor for measuring a position of the tool in three dimensions, and at least one set key. A processor and at least one display device are associated with the handheld surgical tool and configured to display a target trajectory of the handheld surgical tool for the surgical procedure.

21 Claims, 6 Drawing Sheets

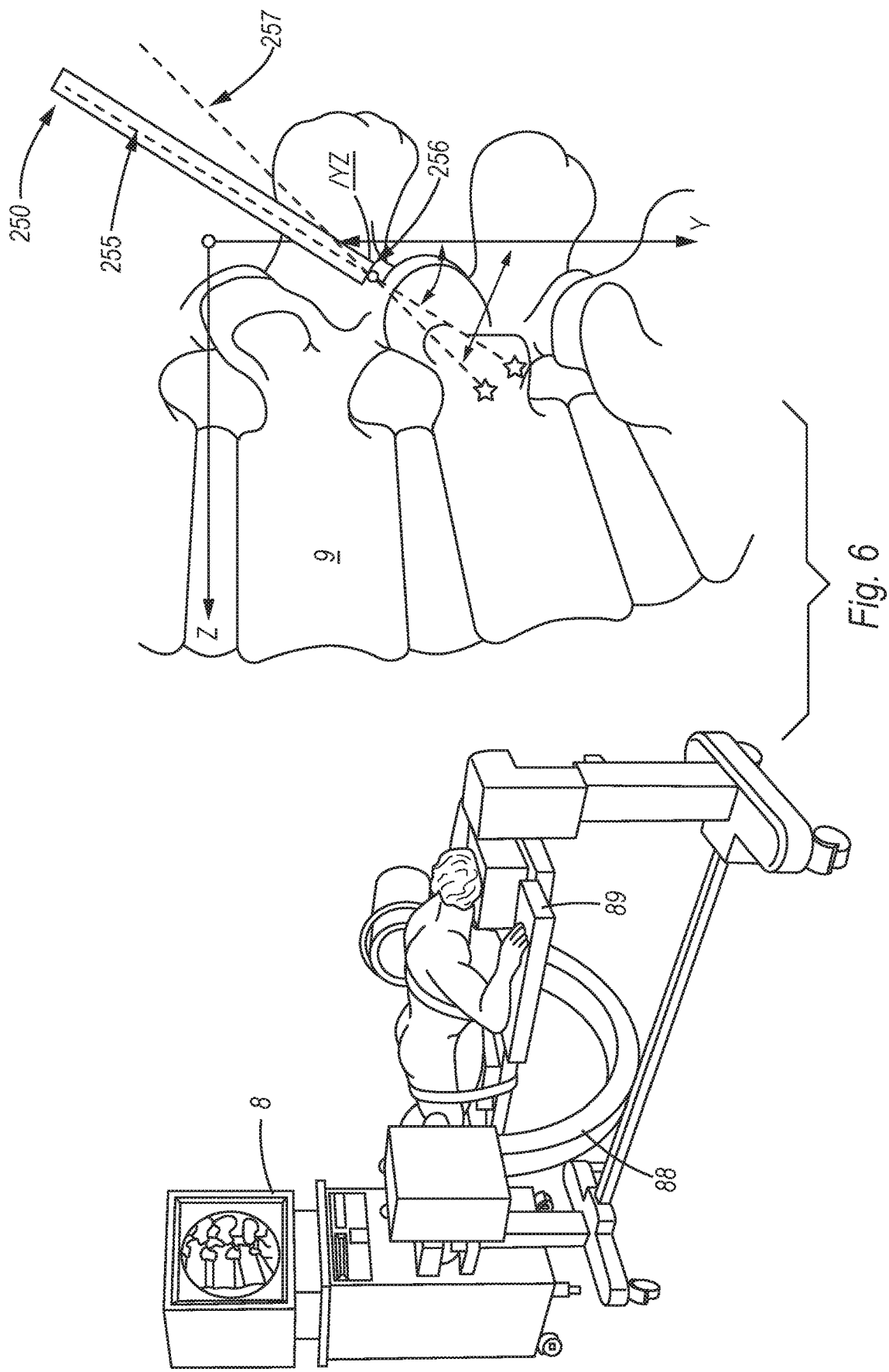

SYSTEM AND METHOD FOR POSITIONING A SURGICAL TOOL

CROSS-REFERENCE TO RELATED APPLICATION

This Application claims priority to U.S. Provisional Patent Application No. 62/763,491, filed on Jun. 15, 2018, the entirety of which is incorporated herein by reference.

FIELD OF THE INVENTION

The invention relates to a surgical navigation system having a handheld surgical tool with computer-aided navigation. The handheld surgical tool comprises a housing, an instrument shaft and a sensor unit, the housing comprising at least one set key and a position memory configured to store a data set for a position upon activation of the at least one set key.

BACKGROUND OF THE INVENTION

Surgery is moving from "open" methodologies, which use direct vision for implant placement, to less invasive techniques, which rely upon fluoroscopic control or sophisticated navigation techniques to guide implantation. The increasing interest in these less invasive procedures has contributed to greater use of fluoro, or alternatively, large capital investments in computer or robot assisted navigation systems.

For fine scale surgery, e.g., for placing implants at a spinal column, a high degree of positional accuracy is required. However, with minimally invasive surgery, direct visual control typically used for the positioning of instruments used by the surgeon is rather difficult. Sufficient visual control can often only be achieved by use of dedicated equipment, such as picture generating devices providing fluoroscopic control and/or sophisticated navigation systems forming a part of the operating room. However, such sophisticated navigation systems are expensive, complex to operate, and as a result sparingly used.

C-arm devices, on the other hand, are more readily available and surgeons are accustomed to their usage. However, continued use of the C-arm device subjects both the surgeon and the patient to a high radiation dose due to repeated X-ray exposure. Further, most C-arms have only one direction of view and consequently require intraoperative repositioning quite often, which can be detrimental to positional accuracy, unduly time consuming, and increases the risk of infection. Biplanar fluoroscopy may also be used, but images must be taken in each plane independently, and as adjustments to desired trajectory are made in one plane, an additional image must be taken in the other to ensure the appropriate heading is not lost. As a consequence, repetitive "back and forth" is needed when using conventional or biplanar fluroscopic control. The result can be high radiation doses, frustration, and longer than desired surgery times.

In order to attempt to address at least some of the above problems, U.S. Pat. No. 8,057,482 B2 describes a handheld surgical tool with certain navigation features that are provided to improved positional accuracy. The tool features a button which has to be pressed when the device achieves its basic reference position, which zeros the tool. Once this is accomplished, the tool can be freely manipulated by the surgeon, and it will show its positioning in space on three numerical displays provided at its casing. The displays show three-dimensional angular orientation of the tool in space. This device generally improves a surgeons ability to determine positioning of the tool in an area with limited access, and consequently restricted visual observance. However, it can be rather difficult for the surgeon to control the plurality of displays in order to check whether a desired orientation has already been reached or is maintained.

SUMMARY OF THE INVENTION

It is an object of the invention to provide an improved surgical navigation system which is easy to operate and that provides more accurate surgical procedures. The invention further relates to a corresponding methods.

According to an aspect of the present invention, the surgical navigation system includes a handheld surgical tool with computer-aided navigation, an imaging device (e.g., a C-arm machine), an alignment module/device, and a user interface module. The imaging device is a device capable of taking two-dimensional images of a patient. The alignment device includes at least one sensor unit, comprising at least one sensor for sensing positional data of the imaging device. The alignment device may be attached to the imaging device and record positional data of the imaging device.

The handheld surgical tool comprises a housing, an instrument shaft and a sensor housing, the sensor housing comprising at least one sensor unit for sensing positional data. The housing comprises a computing unit configured to determine a position of the tool in space based on signals of the sensor unit, at least one set key, and at least one control key. The housing may also include a position memory configured to store data sets corresponding actual positions of the handheld surgical tool and target positions of the handheld surgical tool upon activation of the at least one set key. Alternatively, the position memory may be housed externally to the housing—for example, in a separate device like a separate computer, hard drive, etc. Either way, the computing unit is provided with at least one processor operatively connected to the position memory, the processor being configured for comparing an actual position of the surgical navigation system against at least one position stored in the position memory.

The processor is configured to operate in at least two different modes and for generation of deviation signals. In the first mode, the position of the handheld surgical tool is measured in two dimensions (i.e., within a single plane). In the second mode, the position of the handheld surgical tool is measured in three dimensions. The first mode may be carried out in two or more planes, the two or more planes being non-parallel to one another. Preferably, two of the two or more planes are orthogonal to each other. Deviation signals may be generated, which represent a deviation of the handheld surgical tool in either two or three dimensions in comparison to a predetermined or selected position.

The surgical navigation system may further include a user interface module. The user interface module may be supplied with the actual location of the handheld surgical tool, the deviation signals, and patient images taken by the imaging device. The user interface module includes at least one computer and a visual display that is configured to indicate the location of the handheld surgical tool direction in two or three dimensions, the deviation of the handheld surgical tool in two or three dimensions, and a magnitude of any such deviation. The user interface module may be further configured to overlay images of the patient with the actual location of the handheld surgical tool, a desired location for the handheld surgical tool or combinations thereof, and display such images.

The term "position in space" and its short form "position" in context of the present invention generally refers to a system with six degrees of freedom that may comprise absolute location and orientation. The location might be represented as coordinates of a three-dimensional space with perpendicular axes (e.g. X, Y, Z), while the orientation might be provided by Euler angles (e.g., yaw, pitch, and roll; alpha α, beta β, and gamma γ; phi φ, theta θ, and psi ψ) or by quaternions. According to embodiments of the present invention, the "position" may refer to a simplified position, which includes only the yaw and/or pitch of the tool.

By means of definition, a coordinate system for the human body may be defined featuring an X-axis as side to side (left to right, right to left), a Y-axis as up and down (feet to head, head to feet), and a Z-axis (front to back, back to front) orthogonal to the X- and Y-axis indicating depth. Thereby, an anterior—posterior view provides information regarding a trajectory relative to the X-Y plane.

The "instrument shaft" may be an actual instrument itself. However, it may also be configured as an attachment point enabled to receive an instrument in an interchangeable fashion.

Aspects of the invention provide a processor, having instructions stored on a non-transitory computer readable medium, that when executed by the processor, cause the processor to operate in two distinct operating modes, wherein in one of the two distinct operating modes a reduced position indication is processed. The reduced position indication is a position indication which lacks at least one indication for one degree of freedom compared to the full position indication of the second operating mode. For example, in Euclidean space three angle indications can be used to describe an orientation of a device in a three-dimensional space. But if the absolute location does not need to be monitored, then two, instead of three, of the angles may be monitored, which will not provide a fully fixed orientation, but will instead retain one degree of freedom. If, for example, angles for roll, pitch and yaw are used, than an incomplete position indication could only have indications roll and yaw for example, leaving pitch as a degree of freedom. As another example, if only two rather than three angles are to be used (e.g., if roll is to be ignored), a full position indication will have both angles (e.g., pitch and yaw), whereas an incomplete position indication would indicate only one angle (e.g., yaw only).

In its first operation mode the processor is configured to compare an actual position of the handheld surgical tool against an incomplete position indication stored in the position memory. The processor detects whether a present position of the handheld surgical tool is in conformity with the stored incomplete position indication, and if it is not it will provide a deviation signal. In the above mentioned simplified example using just two angles, the incomplete position data only comprises yaw. By pressing at least one of the control keys, the position may be virtually changed (e.g., the yaw angle may be modified). By pressing of a set key the position will be stored in the position memory as an incomplete position indication. The processor will then detect any deviation from the stored value for yaw, while pitch is still freely modifiable. The user may reposition the tool such that its actual yaw angles matches the stored one. By virtue of this, yaw angle of the tool can be locked in.

After the first angle (e.g., yaw) is set, the first operating mode is used again for a different angle (e.g., pitch). For example, once the yaw angle is locked in, the processor detects whether a present position of the handheld surgical tool is in conformity with the stored incomplete position indication for the other angle, and if it is not it will provide a deviation signal. By pressing at least one of the control keys, the position may be virtually changed (e.g., the pitch angle may be modified). By pressing of a set key the position will be stored (i.e., locked in) in the position memory as an incomplete position indication. The processor will then detect any deviation from the stored value for pitch, while yaw is still freely modifiable. The user may reposition the tool such that its actual pitch angles matches the stored one. By virtue of this, pitch angle of the tool can be locked in.

The processor may also be configured to suppress indicating a deviation signal below a preset threshold. For example, a tolerance threshold may be preset or inputted into the system, provides a certain tolerance around the correct position. Thereby, an over sensitive operation may be avoided. As an example, an acceptable deviation of up to two degrees may be allowed without indicating a deviation.

In this first operation mode the indication of at least one spatial dimension is suppressed. This means, for example, that no pitch angle information will monitored or be displayed in a first step, thereby leaving a yaw angle only indication. In a second step, no yaw angle information will monitored or be displayed. Surprisingly, by reducing the amount of information displayed, namely by suppressing indication of the spatial dimension by which the first operation mode is reduced, the display presented to the operator is simplified. This provides a better concentration on relative orientation aspects. In other words, the reduction of the display by said at least one spatial dimension prides a benefit to the operator in maintaining proper positioning. Additionally, by separately locking in the angles (e.g., yaw and pitch), a desired three-dimensional angle can be more easily and properly obtained.

Upon user command (e.g., by a further actuation of the set key) or automatically, the processor will be switched from the first to the second operation mode after the required angles have been locked in. In its second operation mode, the processor utilizes the full position indication. In the above example, this will bring both the pitch and yaw angle into consideration. In this operating mode, the processor checks yaw angle as well as pitch angle against the values stored in the position memory. In this case, the user interface module shows indications in all those angles monitored by the processor.

By virtue of this, the surgeon can precisely acquire a position corresponding to a given track by orienting the surgical tool in a three-step fashion. In the first step, according to the example, the surgeon needs to concentrate on positioning of the tool in one plane only, and sets this position (e.g., yaw) by pressing the set key. In a second step, the surgeon may then concentrate on positioning the tool in a second plane, and sets this position (e.g., pitch) by pressing the set key, and while doing so he is of no risk of losing the yaw position as the processor has already locked in this angle. If the desired position in the other plane (in the example: pitch) is achieved, then the full position will be locked-in (e.g., by a further actuation of the set key). In essence, the surgeon needs to concentrate on achieving one orientation at a time only, as the processor is monitoring positional data in a single plane at a time. At no time is the surgeon at risk of losing a position once achieved, since the tool itself keeps track of any deviation and thus allows the surgeon to regain the set position. In the final step, once a three-dimensional angle is set (e.g., based on the set yaw and pitch), the processor operates in the second mode and monitors positional data in three dimension and provides deviations of the tool relate to both angles (e.g., yaw and pitch).

According to one illustrative example, the surgeon might position the tool in a first plane that is defined by the imaging device. For example, the first plane might be the anterior-posterior plane, where an x-ray image is generated by a correspondingly orientated C-arm. With the help of the generated picture, the surgeon might define the desired starting point and the desired trajectory of the tool in this plane using known anatomic landmarks visible on the generated picture. By operating the control keys and the set key the surgeon can then freeze the trajectory in the anterior-posterior plane. Afterwards the C-arm is rotated so that the picture generated shows, for example, the lateral plane. The surgeon might then define the desired trajectory of the tool in this plane. While doing this, the tool helps the surgeon by keeping the correct orientation in the anterior-posterior plane, as previously defined. Once he has found the correct trajectory in the lateral plane, he might freeze this as well by pressing a set key on the tool. After this, the desired trajectory is fully defined and the inventive tool supports the surgeon to maintain its correct orientation without requiring any further picture generation.

It is much easier to manipulate a surgical tool in successive planes so as to provide final control in three-dimension space, as compared to instruments according to the state of the art which lacks any locking-in features. As a result, the surgical tool according to the present invention is much easier to handle.

The user interface module can be configured to show the deviation qualitatively. According to embodiments, the user interface module is configured to provide visual indications. Providing a non-numerical indication alleviates the surgeon from the task of interpreting a numerical reading and comparing it against any target number which requires considerable mental capacity. This is even truer if three numerical indications have to be kept under control at once, as it was necessary according to the prior art. Providing a non-numerical indication gives an easy cue to the surgeon whenever deviations occur, without requiring him to perform mental calculations. An example for such non-numerical deviation indication includes a "bullseye" display with a crosshair, wherein a center of the bullseye corresponds to the desired trajectory.

Additionally indications can be provided by the system, including aural and/or tactile indications. An example for an aural indication is a variably pitched tone for an indication in one direction; further, tone pauses can be used, like providing a continuous tone in the correct position and a dash like tone sequence for deviations to one side and a dot like sequence for a deviation to the other side, merging into a continuous tone upon reaching the correct position. Example for a tactile indication are vibrating elements placing on each side of the housing of the tool, thereby signaling the operating surgeon in a very intuitive manner to which direction a deviation occurs; the vibrating will stop upon reaching the correct position.

Further, the user interface module may comprise a hybrid display with other (e.g., fluoroscopic) imagery of the patient, so that the positional relation of the surgical tool to the patient can be seen directly.

The user interface module, the alignment module, and/or the handheld surgical tool may be configured to supply positional data of the handheld surgical tool to an external system (e.g., an operating theatre navigation system). The user interface module may also be configured to drive a remote display, preferably using Bluetooth®, WiFi, or MirrorLink technology.

The handheld surgical tool may be configured with a rechargeable battery and a wireless charging unit. In such an embodiment, no external contacts would be required for powering of the surgical tool, thereby facilitating cleaning of the surgical tool after use.

The at least one set key and/or control key of the surgical tool can be configured as a momentary switch, a sensor switch, or a voice controlled switch. For example, a conventional momentary switch acting mechanically may be employed. Alternatively, a sensor switch may be advantageously provided, which does not need to have moveable contact and can be cleaned easily. A voice control switch can also be used so that the surgeon does not have to press a switch or place his finger on a sensor surface. Instead it will suffice to speak out loudly a certain phrase, like "Freeze" in order to achieve a desired action.

In a preferred embodiment, the sensor unit(s) are selected from a group comprising accelerometers, rate gyroscopes, and magnetometers, all preferably having at least a 3-axis configuration.

The handheld surgical tool may comprise a status indicator, e.g. a status LED. The status indicator might indicate whether the tool is switched on, whether the battery level is low and/or in case there is communication with, for example, the user interface module, a feedback device, or another external system.

The invention further relates to methods for carrying out computer aided surgical procedures.

BRIEF DESCRIPTION OF THE DRAWINGS

The following description, given by way of example and not intended to limit the invention to the disclosed details, is made in conjunction with the accompanying drawings, in which like references denote like or similar elements and parts, and in which:

FIG. 6 further illustrates components of a surgical navigation system during a second operating step, according to embodiments of the invention.

DETAILED DESCRIPTION OF THE INVENTION

Detailed embodiments of the present surgical navigation system, and corresponding methods, are disclosed herein. However, it is to be understood that the disclosed embodiments are merely illustrative of a surgical navigation system, and of methods, that may be embodied in various forms. In addition, each of the examples given in connection with the various embodiments of the systems and methods are intended to be illustrative, and not restrictive. Further, the drawings and photographs are not necessarily to scale, and some features may be exaggerated to show details of particular components. In addition, any measurements, specifications, and the like shown in the figures are intended to be illustrative, and not restrictive. Therefore, specific structural and functional details disclosed herein are not to be interpreted as limiting, but merely as a representative basis for teaching one skilled in the art to variously employ the present system and methods.

Figure 1:
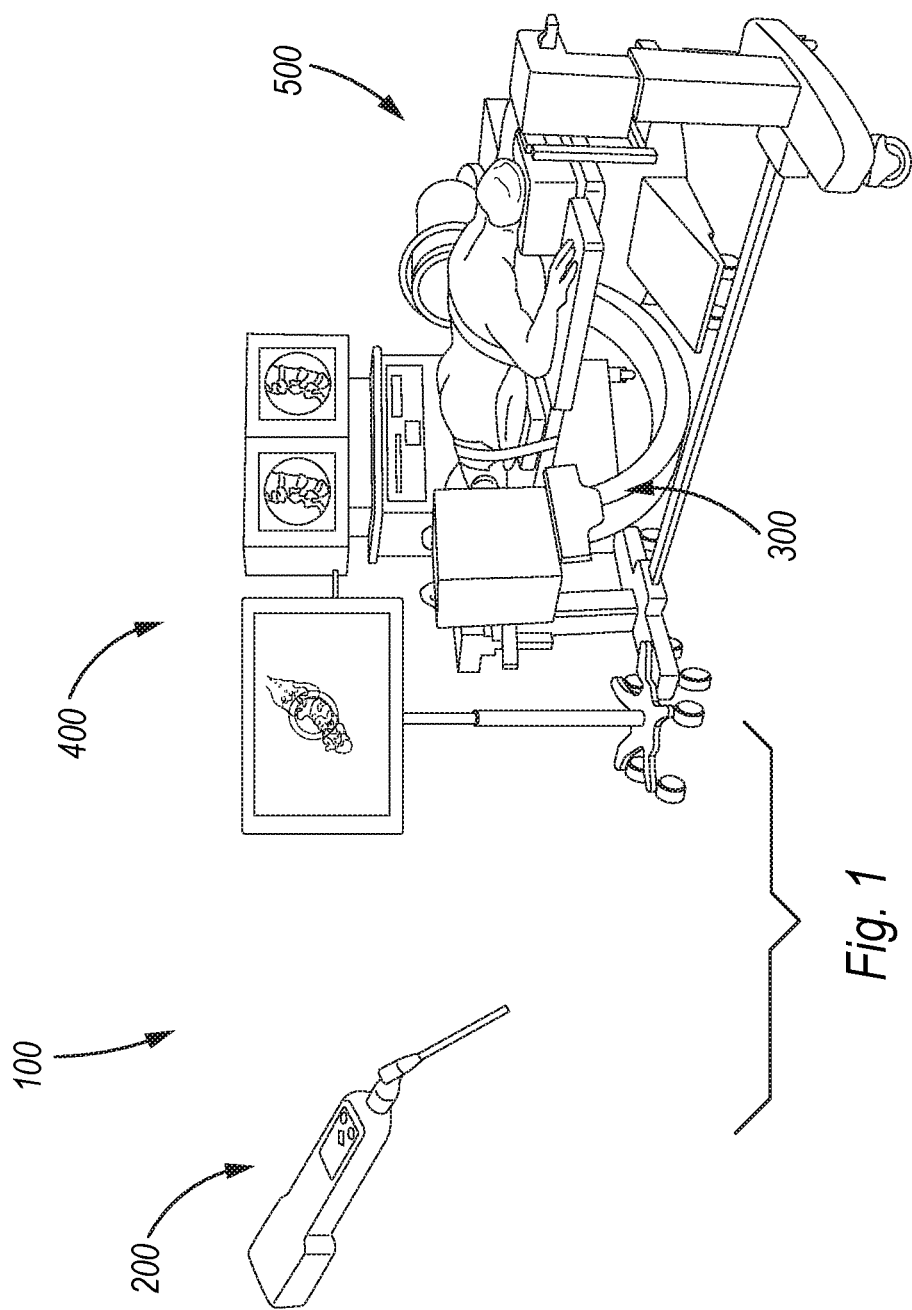
FIG. 1 illustrates the various components of a surgical navigation system, according to embodiments of the invention.

With reference to FIG. 1, an embodiment of a surgical navigation system 100 of the present invention is illustrated. The surgical navigation system 100 comprises a handheld surgical tool 200, an alignment module 300, a user interface module 400, and an imaging device 500. As illustrated by FIG. 1, the surgical navigation system 100 is located within a surgical space and configured to be implemented by a surgeon carrying out a surgical procedure on a patient.

A preferred embodiment for alignment module 300, according to the present invention, is illustrated in FIG. 1. Alignment module 300 includes components similar to those described below with regard to handheld surgical housing 200. In particular, alignment module 300 includes the necessary sensors, processors, and communication means for determining and communicating position information of imaging device 500.

Figure 2A:
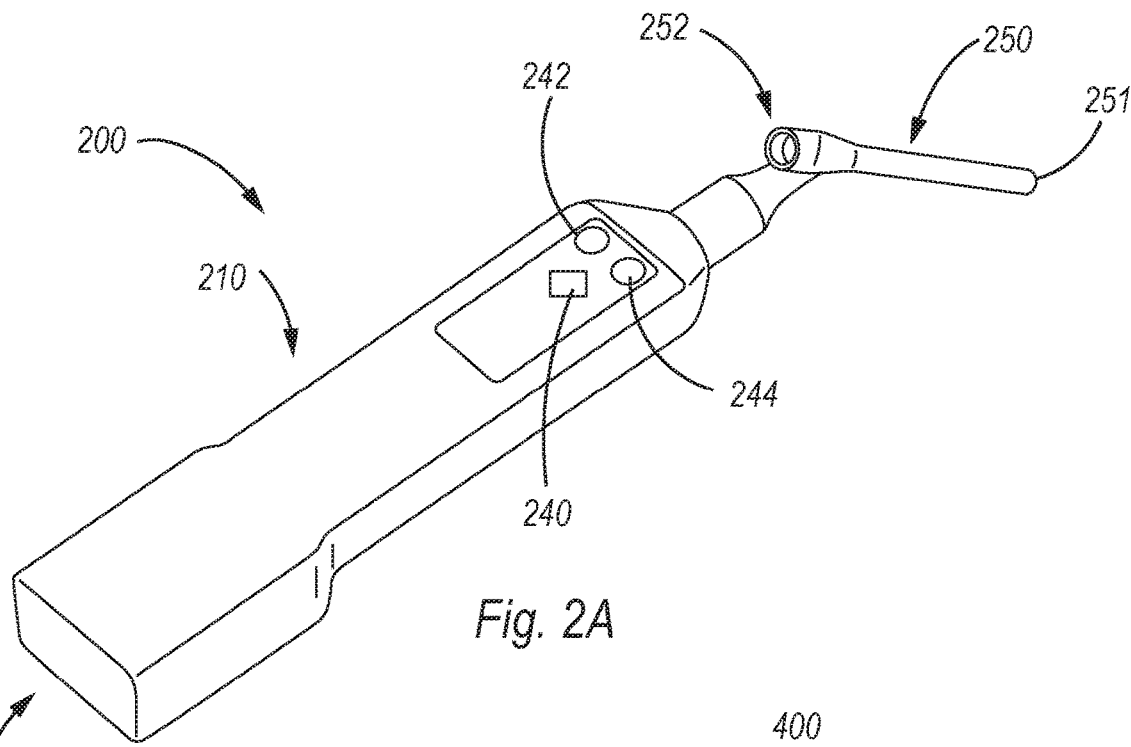
FIG. 2A illustrates a perspective view of a handheld surgical tool, according to embodiments of the invention.

A preferred embodiment for a handheld surgical tool according to the present invention is shown in FIG. 2A. The surgical tool, comprises: a housing 210, an instrument shaft 250, and a sensor housing 260. The instrument shaft includes a distal end tip 251 and a proximal end 252. The instrument shaft 250 in this depicted embodiment is a wire guide having an internal hollow conduit for guiding a surgical wire to be placed at a bone. In order to place the surgical wire in a correct manner, the wire guide must be placed with its tip on the target location in a certain orientation, which determines the angle with which the wire will enter the bone material. The wire guide may be exchanged against other instruments if desired.

The sensor housing 260 is releasably connected to the housing 210. It is to be noted that such a detachable configuration is an option and sensor housing 260 may well be integrated into housing 210.

Figure 2B:
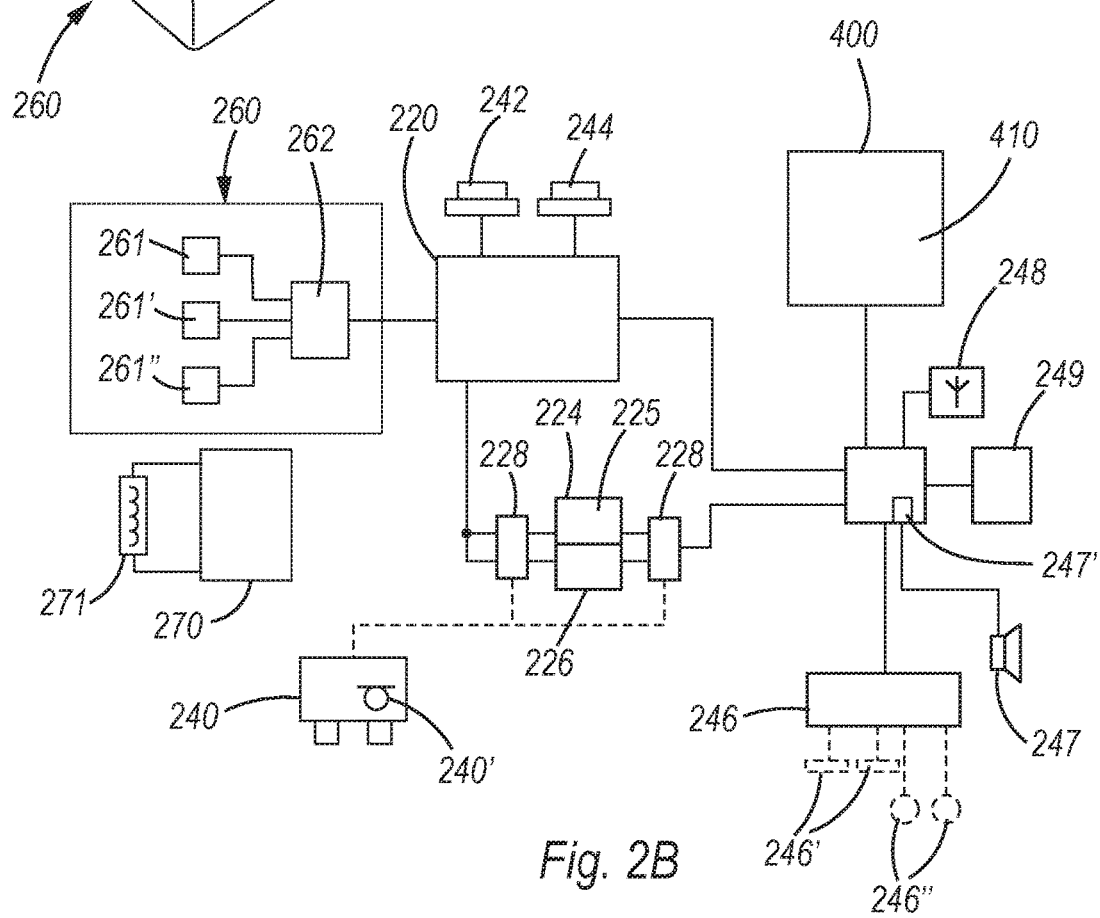
FIG. 2B illustrates a schematic view showing function blocks of elements of a surgical navigation system, according to embodiments of the invention.

A functional explanation of the handheld surgical tool 200 according to a preferred embodiment will be given with reference to FIG. 2B. The sensor housing 260 comprises at least one (in the depicted embodiment three different) sets of sensor units 261, 261', 261", the sensor units being a 3-axis accelerometer, 3-axis rate gyroscope and a 3-axis magnetometer, respectively. Each sensor unit 261, 261', 261" on its own produces positional information independently from each other, said positional information comprising, for example, acceleration or other positional data from yaw, roll, and pitch reference to the body frame of the handheld surgical tool. The three sensor units 261, 261', 261" are connected to a data fusion module 262 configured to process the output signals of the sensor units in a generally known manner (filtering, normalizing, calibrating, etc.) and further to merge the processed signals in order to produce a unified consolidated position output signal. For this merging, generally known techniques may be used (like Kalman-filter, Quaternion-gradient, complementary filter, etc.). Optionally, the data fusion module 262 is further configured to code the output by Quaternions in order to avoid singularities, such as gimbal lock issues. According to an alternative embodiment, data fusion module may be incorporated into processor 220.

The consolidated output position signal of the data fusion module 262 is supplied to processor 220. Based on this signal a conversion to Euler angles or 3D vectors is performed by successive projection on the planes of a 3D-Euclidean space, thereby forming a trajectory definition. The trajectory definition which is defined by, for example, angles for yaw and pitch can be stored in a position memory 224. In one embodiment, the output position signal includes data based on quaternions, which is subsequently converted to 3D vectors and from there to 2D vectors. The trajectory is then adjusted successively in relation to two of the 2D vectors to arrive at a final 3D vector.

The position memory 224 may comprise a first memory unit 225 and a second memory unit 226. The memory units 225, 226 may be configured to selectively store different positional data. According to one embodiment, memory unit 225 selectively stores positional data related to a single plane (e.g., an X-Y plane corresponding to yaw) while memory unit 226 selectively stores positional data related to a different single plane (e.g., an Y-Z plane corresponding to pitch). In another embodiment, the position memory 224 stores positional data related to a single plane and a single 3D vector, which data is then translated into a second 2D vector. Storing and recalling of data into and from the first and second memory unit 225, 226 may be controlled by a selector 228 which is operatively connected to set key 240 which is further connected to processor 220. Alternatively, a single memory (i.e., position memory 224) may be utilized, which stores all of the positional data.

As an alternative to the set key 240, a microphone 240' may be provided. Thereby, a voice activation could be substituted for physical pressing of the set key 240. Speaking a command word like "freeze" may thus substitute pressing of the set key in order to lock in yaw/pitch as desired.

The processor 220 is operatively connected to the position memory 224, the set key 240, and to left and right control keys 242 and 244. Further, processor 220 is configured to recall data from the first memory unit 225, the second memory unit 226, or position memory 224 generally, depending on an operation mode. The processor 220 is configured for two operation modes, which may be selected by activation of the set key 240. In a first operation mode, the processor 220 is configured to recall stored incomplete position from the first memory unit 225, the second memory unit 226, or position memory 224 generally, and to compare it against an actual position indication as supplied by the sensor units 261. Based on the difference between these position indications, the processor 220 generates a first deviation signal for one direction, such as yaw (or for another direction, such as pitch). In the second operation mode, the processor 220 is configured to recall the full position indication from a combination of the first and second memory units 225, 226 (or position memory 224) and to compare it against the actual position indication as supplied by the sensor units 261. Based on the difference between these position indications it generates a different deviation signal which has one more dimension than the first deviation signal, such as yaw and pitch in the preferred embodiment. Switching from the first to the second operation mode is controlled by the user by means of set key 240, as will be more fully described below. Although certain embodiments herein describe the deviation signals being generated and supplied by processor 220, the invention is not so limited. For example, processing of positional data may be carried out by the user interface module, the handheld surgical tool, or combinations thereof.

Further, a user interface module 400 is provided to which the deviation signals are supplied (or generated). User interface module 400 may comprise at least one computer having at least one processor, at least one display 410, and optionally at least one memory unit for storing data (e.g., positional data from the handheld surgical tool 200). The user interface module 400 is configured to indicate direction—and in a qualitative manner magnitude—of any deviation as defined by the deviation signals. The user interface module 400 may include a visual indicator, the visual indicator being formed by a display 410. The display 410 forming the visual indicator, according to embodiments, comprises a bullseye display with in a crosshair pattern (see FIGS. 3 and 5).

According to one embodiment, the handheld surgical tool 200 may include a tactile indicator 246, an aural indicator 247, or both. The tactile indicator 246 comprises two pairs of vibration transducers 246' and 246" arranged on opposite lateral sides of the housing 210 and on the top and bottom side of the housing 210, respectively. As an aural indicator, a loudspeaker 247 is provided which is driven by a sound module 247' forming a part of either the handheld surgical tool 200 or the user interface module 400. Further, the handheld surgical tool 200 is configured with a wireless transmitter 248 configured for communication with alignment module 300 and user interface module 400.

Further, handheld surgical tool 200 may include a separate processor 249 for calculating an offset. It is configured to determine the position of a tip 251 of the instrument shaft 250 attached to housing 210. Data regarding a distance between a tip 251 and the sensors 261, 261', 261" of the handheld surgical tool 200 and the angle at which instrument shaft 250 is orientated relative to housing 210 may be calculated by processor 249 and stored in an associated memory. Thereby processor 249 is enabled to modify position indications of the sensors 261, 261', 261" such that it is the position of the tip 251, rather than a position sensors 261, 261', 261" is used by the surgical navigation system. The offset is adjusted for each instrument shaft utilized by the handheld surgical tool. According to an alternative embodiment, processor 220 is configured to calculate the offset.

A rechargeable battery 270 is provided which supplies the various components of the handheld surgical tool. The supply lines are not shown FIG. 2B. In order to recharge the battery 7 a recharging coil 271 is provided which is configured for wireless charging.

Embodiments for performing methods of computer aided surgery, as carried out by the aforementioned components will now be described.

First, the surgical navigation system need to be set up within the operating room. In order to do so, the alignment module 300 is preferably attached to imaging device 500. According to one preferred embodiment, imaging device 500 takes the form of an X-ray imager (e.g., C-Arm). Attachment may be accomplished via any suitable manner (e.g., via fasteners, magnets, etc.). As FIG. 1 illustrates, imaging device 500 is located next to the patient that is located on an operating table. User interface module 400 is similarly positioned within the operating room, near the operating table, for viewing by the surgeon.

Next, handheld surgical tool 200 may be assembled (or come preassembled). According to one preferred embodiment, the housing 210 of handheld surgical tool 200 is sterile packed and designed for single use. A sterile pouch is opened, a lid is removed from the back of the housing 210, and the sensor housing 260 is inserted until fully engaged and flush with the housing 210. The lid may then be closed, sealing the sensor housing 260 within the housing 210.

A desired instrument shaft 250 (i.e., end tool) is chosen (e.g., a guide for guidewire preparation or a guide for pilot hole preparation), and attached to a proximal end of housing 210, preferably via a quick connect post. The invention is not limited to any one particular end tool, and the proximal end of housing 210 is configured to accommodate multiple different types of end tools using a universal or common connection.

The alignment device 300 and handheld surgical tool 200 may then be activated. By way of example only, removal of a pull tab on handheld surgical tool 200 will enable battery 270 to power on the components handheld surgical tool 200, while a switch on alignment device 300 may be toggled in order to activate it. Preferably, this is done prior to draping the imaging device 500.

The connection (e.g., wireless) between the alignment module 300 and user interface module 400 may then be verified (e.g., by moving a part of the X-ray imager (e.g., slightly rotating the rainbow of the C-Arm)) and confirming that a corresponding icon on display 410 of user interface module, moves. The imaging device 500 is then positioned in a patient oriented plane (e.g., an AP plane) for later space matching. In one embodiment, this includes an initial calibration to understand the orientation of the imaging device 500, after which space matching is performed to match the virtual space of the imaging device 500 with the main instrument (e.g., the instrument shaft 250 attached to housing 210).

The connection (e.g., wireless) between the handheld surgical tool 200 and the user interface module 400 is activated (e.g., by keying in a code indicated on the handheld surgical tool 200), and the connectivity may be verified (e.g., by moving a part of the handheld surgical tool 200) and confirming that a corresponding icon (e.g., a handle icon) on display 410 moves at the same time.

Aspects of the procedure (e.g., surgical level, screw type, and implant side) are pre-stored or provided to the user interface module 400 and/or handheld surgical tool 200. For example, based on provided aspects of the desired surgical procedure, default values for starting target angles appropriate for the intended surgery are inputted. For example, the user interface module 400 and/or handheld surgical tool 200 is programmed with default target angle values (e.g., from research, published sources, or preoperative imaging data) for each type of surgery, that approximate the angles with which the surgical too will need to be oriented for an effective surgery. This eliminates or minimizes the amount of adjustment (in other steps, described below) needed to establish a trajectory for the actual surgery—such as by allowing the initial trajectory to be within a crosshair on the display 410 of the user interface module 400. For example, a left sided transfacet pedicle screw default value, based on the literature, would be directed 15 degrees laterally and 30 degrees caudally.

Next, handheld surgical tool 200 is calibrated to the surgical navigation system. According to a preferred embodiment, an alignment sleeve (or the like) is placed on the shaft of the handheld surgical tool 200 (not shown). According to one embodiment, the alignment sleeve is held against the back of the patient and an indication (e.g., a line) is marked (e.g., with a provided marking pen) on the patient's skin adjacent (e.g., along) the sleeve. Preferably, the line is marked as parallel as possible to where the implantables (e.g., screws) are to be placed (e.g., as parallel as possible to the spinous process). According to an alternative embodiment, the line can be marked as orthogonal as possible to where the implantables are to be placed (e.g., as orthogonal as possible to the spinous process), and the software of the system can convert the orthogonal configuration to parallel for use in the alignment processes. The marked line is tested (i.e., to see if the marked line can be relied upon as a reference point). Testing is preferably accomplished by, e.g., lifting the instrument and then repositioning it along the marked line). The line is confirmed (e.g., by pressing set key 240, or by a surgical team member or representative clicking a button on user interface module 400).

Alternatively, an alignment sleeve (or the like) is adjustably fixed to a known reference point in real space relative to the patient (e.g., fixed to the operating table). For example, the sleeve can be fixed to a clamp is that is fixed to the operating table. The sleeve may be fixed as parallel as possible to the spinous process of the patient. In certain embodiments, the trajectories generated by system are determined relative to the spinous process of the patient, and as such, the closer the sleeve is to parallel with the spinous process of the patient, trajectory corrections, if any, can be fewer in number and/or lower in magnitude. According to an alternative embodiment, the sleeve can be fixed as orthogonal as possible to where the implantables are to be placed (e.g., as orthogonal as possible to the spinous process), and the software of the system can convert the orthogonal configuration to parallel for use in the alignment processes. A portion of the handheld surgical tool 200 (e.g., housing 210 or shaft 250) is inserted into the sleeve and alignment is confirmed (e.g., by pressing set key 240, or by a surgical team member or representative clicking a button on user interface module 400).

According to a further alternative embodiment, the handheld surgical tool is placed flat on a table (e.g., the operating table). This defines a zero position and is acknowledged by pressing the set key 240. This sets a body frame of the handheld surgical tool with a reference frame of the operating room.

A final step in the calibration process may include the imaging device taking an image (e.g., in an anterior—posterior (AP) plane) while the handheld surgical tool 200 is held in an alignment position (e.g., along the line marked on the patient). An alignment indicator (e.g., line) on the display 410 is moved (e.g., by virtual dragging) into alignment with the shaft of the handheld surgical tool 200.

This procedure registers the position of the shaft 250 of the handheld surgical tool 200 in real space to its represented position in the virtual space of the system. For example, the yaw of handheld surgical tool 200 is aligned and/or matched with the yaw of alignment module 300 in the virtual space. In certain embodiments, the pitch and roll do not need to be addressed as an accelerometer in handheld surgical tool 200 and the accelerometer in alignment module 300 are similarly affected by the gravity in the operating room.

According to an alternative embodiment, the final calibration step includes the imaging device 500 taking an image (e.g., in an AP plane) while the handheld surgical tool 200 is held in an alignment position (e.g., inserted into the sleeve). An alignment indicator (e.g., line) on the display 410 is moved (e.g., by virtual dragging) into alignment with handheld surgical tool 200 in the image.

This procedure registers the position of handheld surgical tool 200 in real space to its represented position in the virtual space of the system. For example, the yaw of handheld surgical tool 200 is aligned and/or matched with the yaw of alignment module 300 in the virtual space. In certain embodiments, the pitch and roll do not need to be addressed as the accelerometer in handheld surgical tool 200 and the accelerometer in alignment module 300 are similarly affected by the gravity in the operating room.

Once the handheld surgical tool 200 is calibrated, a set of steps are carried out to effectuate a computer aided surgical procedure. As a first step, a distal end (e.g., tip 251) of the shaft 250 of the handheld surgical tool 200 is placed in real space at the starting point on the patient's anatomy (e.g., a defined bony starting point such as, for example, a sulcus created by a high speed burr, or, for example, a screw pocket of an implant). The starting point is preferably registered on user interface module as a point in the virtual space of the system (e.g., preferably, X=0, Y=0, Z=0; that is, the starting point is preferably set as the origin point in the virtual space of the system). Also, a proximal end 252 of the shaft 250 is registered as a point in the virtual space of the system relative to the starting point in the virtual space of the system, so that the orientation of the shaft 250 in real space relative to the starting point in real space, and relative to the default target angle/trajectory/orientation, is determinable and representable by the system in the virtual space of the system. Then, the handheld surgical tool 200 can be and is moved in real space to angulate the shaft 250 about the starting point in real space until the display 410 indicates that the orientation of the shaft in real space relative to the starting point is aligned with the default target angle/trajectory/orientation.

Figure 3:
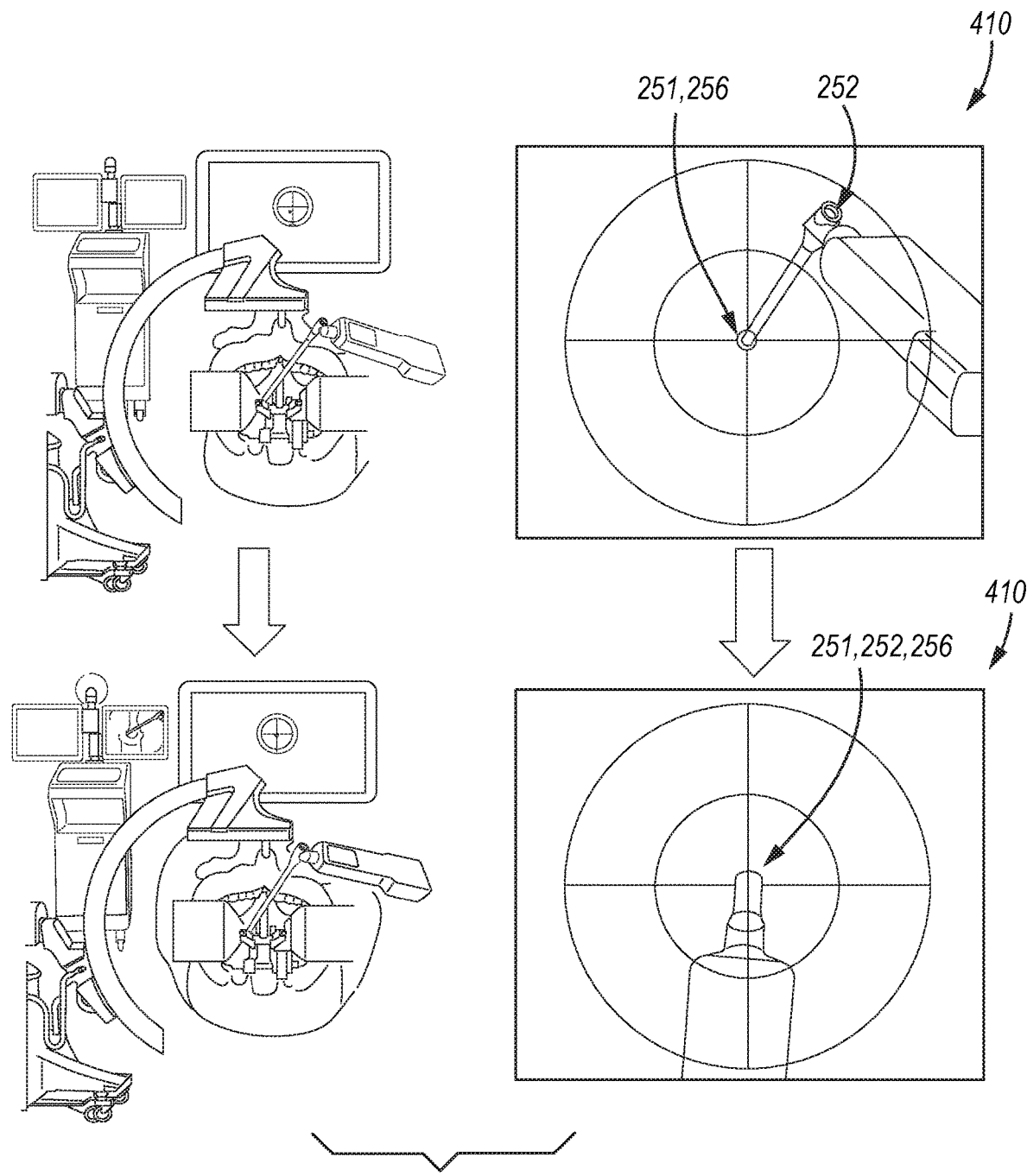
FIG. 3 illustrates components of a surgical navigation system during a first operating step, according to embodiments of the invention.

For example, as illustrated by FIG. 3, the imaging device 400 (e.g., C-arm) is oriented to take an AP x-ray image. The predefined trajectory for this plane is recalled from an associated memory (e.g., positional memory 224) and handheld surgical tool 200 is moved in real space and a position of an indicator on display 410 (e.g., a green dot representing a proximal end 252 of the shaft) is shown relative to a position of a target point (e.g., distal tip 251 corresponding to the center of a bullseye's cross-hairs), and when the positions are aligned, the system has determined that the shaft 250 is oriented in real space, relative to the starting point, in alignment with the default AP target angle (e.g., an established AP trajectory based on the literature or preoperative imaging data), and the display 410 alerts the user to the alignment (e.g., by changing the GUI color to predominantly green). When the positions are aligned, preferably an AP X-ray image is taken by the imaging device 500. If necessary—for example, if the distal end of the shaft (i.e., the center of rotation of the shaft about the starting point) is difficult to see on the X-ray image, such as if the implant is overlapping the distal end of the shaft on the X-ray image—this step can be repeated a number of times to allow the system (e.g., the software of the system) to register different angles/trajectories/orientations of the shaft 250, and use those angles/trajectories/orientations to calculate the location of the distal end of the shaft and calculate the center of rotation of the shaft about the staring point. This center of rotation determination can additionally or alternatively be accomplished manually (e.g., through a drag-and-drop interface), or by feature recognition.

Figure 4:
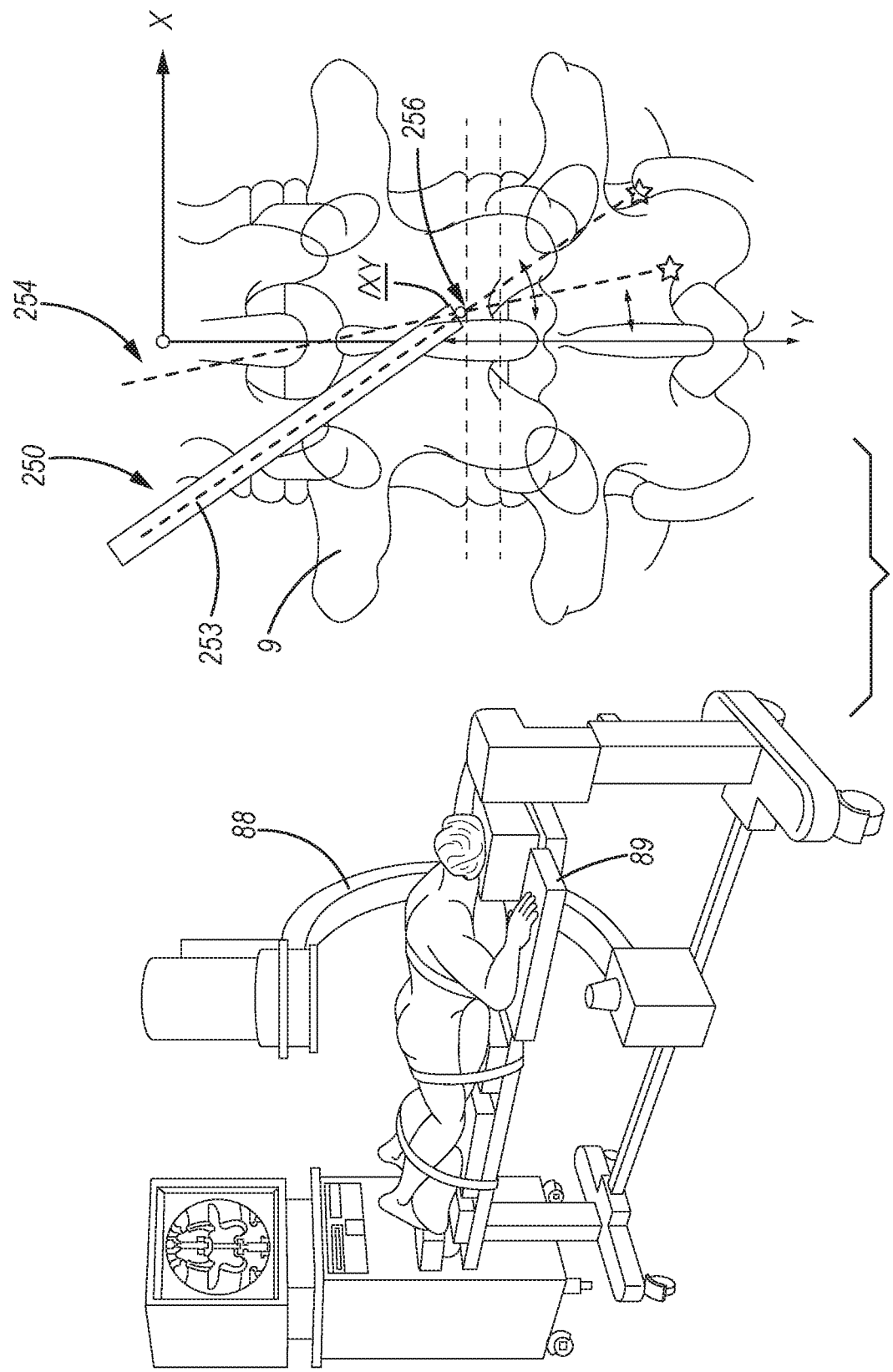
FIG. 4 further illustrates components of a surgical navigation system during a first operating step, according to embodiments of the invention.

Once aligned, and after the x-ray image is taken, the image is provided on display 410, as illustrated by FIG. 4. The AP X-ray image shows the relevant anatomy and the shaft 250 of handheld surgical device 200. The display 410 additionally indicates, on the AP X-ray image, the AP angle of the orientation 253 of the shaft (e.g., by a line along the longitudinal axis of the shaft). As discussed above, the AP angle/trajectory/orientation shown is the default AP angle/ trajectory/orientation, as confirmed by the GUI in the previous step. Additionally, display 410 presents a relative angle/trajectory/orientation indicator 254 changeable in virtual space (e.g., a line rotatable in virtual space about the starting point 256, corresponding to the location of tip 251). Using left and right control keys 242, 244 (e.g., left and right keys that rotate the indicator line 254 clockwise and counterclockwise about the starting point), the user can change the AP angle/trajectory/orientation of the indicator 254 in virtual space from the default AP angle/trajectory/orientation to a desired AP angle/trajectory/orientation (e.g., referencing anatomic landmarks shown on the AP X-ray image). For example, if the surgeon sees that indicator line 254 does not pass through the appropriate anatomy (e.g., pedicle), the surgeon can change the AP angle/trajectory/orientation of the indicator line 254 until the line passes through the desired anatomy. The display 410 can further indicate (e.g., by the provided stars) the endpoint of the desired trajectory.

Then, preferably, the user can confirm the desired angle/trajectory/orientation, for example, by pressing set key 240. For example, when the surgeon determines that indicator line 254 is at the appropriate AP angle/trajectory/orientation, the surgeon can press set key 240. Upon confirmation, the target AP angle/trajectory/orientation is changed from the default AP angle/trajectory/orientation (e.g., that was taken from research and literature sources) to the desired AP angle/trajectory/orientation (e.g., that has been established by the surgeon). Data for the new target AP angle/trajectory/orientation (i.e., for the desired AP angle/trajectory/orientation) is then saved into position memory 224, and preferably selectively stored in first memory unit 225 or second memory unit 226. The data for the new target AP angle/trajectory/orientation may additionally or alternatively be stored in position memory housed externally to the housing of the handheld surgical tool 200—for example, in a separate device like a separate computer, hard drive, etc. This then locks in the first desired angle/trajectory/orientation. As understood from the previous disclosure, during this process the system is only concerned with, and correspondingly measuring, relative movement in an X-Y plane (e.g., in the AP plane around the Z-axis). The system disregards, and does not measure, relative movement along the Z-axis. This allows, for example, the yaw to be selected and locked-in without regard to other angles or orientations, such as pitch.

Next, distal end (e.g., tip 251) of the shaft 250 of the handheld surgical tool 200 remains in real space at the starting point. The starting point preferably remains registered on the GUI as the origin point (e.g., X=0, Y=0, Z=0) in the virtual space. Also, proximal end 252 of the shaft 250 remains registered as a point in the virtual space relative to the starting point in the virtual space, so that the orientation of the shaft 250 in real space relative to the starting point in real space, and relative to the default lateral target angle/trajectory/orientation (e.g., default target angle/trajectory/orientation in the Y-Z plane), is determinable and representable by the system in the virtual space. The imaging device 400 (e.g., C-arm) is further oriented to take a lateral x-ray image and the predefined trajectory for this plane is recalled from an associated memory (e.g., positional memory 224). Then, handheld surgical tool 200 can be and is moved in real space to angulate the shaft about the starting point in real space until the GUI indicates that the orientation of the shaft in real space relative to the starting point is aligned with the default lateral target angle/trajectory/orientation. For example, as handheld surgical tool 200 is moved in real space, a position of an indicator on the GUI (e.g., a green dot representing a proximal end of the shaft) is shown relative to a position of a target point (e.g., the center of a crosshairs), and when the positions are aligned, the system has determined that the shaft 250 is oriented in real space, relative to the starting point, in alignment with the default lateral target angle/trajectory/orientation (e.g., a lateral trajectory based on the literature or preoperative imaging data), and display 410 alerts the user to the alignment (e.g., by changing the GUI color to predominantly green). When the positions are aligned, a lateral X-ray image in the Y-Z plane is taken. If necessary—for example, if the distal end of the shaft (i.e., the center of rotation of the shaft about the starting point) is difficult to see on the X-ray image, such as if the implant is overlapping the distal end of the shaft on the X-ray image—this step can be repeated a number of times to allow the system (e.g., the software of the system) to register different angles/trajectories/orientations of the shaft 250, and use those angles/trajectories/orientations to calculate the location of the distal end of the shaft and calculate the center of rotation of the shaft about the starting point. This center of rotation determination can additionally or alternatively be accomplished manually (e.g., through a drag-and-drop interface), or by feature recognition.

Once aligned, an x-ray image is taken in a lateral plane (e.g., the Y-Z plane) and the image is provided on display 410, as illustrated by FIG. 6. The lateral X-ray image shows the relevant anatomy and the shaft 250 of handheld surgical device 200. The display 410 additionally indicates, on the lateral X-ray image, the lateral angle of the orientation 255 of the shaft 250 (e.g., by a line along the longitudinal axis of the shaft). As discussed above, the lateral angle shown is the default lateral angle/trajectory/orientation, as confirmed by the GUI in the previous step. Additionally, display 410 presents a relative angle/trajectory/orientation indicator 257 changeable in virtual space (e.g., a line rotatable in virtual space about the starting point 256, corresponding to the location of tip 251). Using left and right control keys 242, 244 (e.g., left and right keys that rotate the indicator line 257 clockwise and counterclockwise about the starting point), the user can change the lateral angle/trajectory/orientation of the indicator 257 in virtual space from the default lateral angle/trajectory/orientation to a desired lateral angle/trajectory/orientation (e.g., referencing anatomic landmarks shown on the lateral X-ray image). For example, if the surgeon sees that indicator line 255 does not pass through the appropriate anatomy (e.g., pedicle), the surgeon can change the lateral angle/trajectory/orientation of the indicator line 257 until the line passes through the desired anatomy. The display 410 can further indicate (e.g., by the provided stars) the endpoint of the desired trajectory.

Then, preferably, the user can confirm the desired angle/trajectory/orientation, for example, by pressing set key 240. For example, when the surgeon determines that indicator line 257 is at the appropriate lateral angle/trajectory/orientation, the surgeon can press set key 240. Upon confirmation, the target lateral angle/trajectory/orientation is changed from the default lateral angle/trajectory/orientation (e.g., that was taken from research, literature sources, and/or preoperative imaging data) to the desired lateral angle/trajectory/orientation (e.g., that has been established by the surgeon). Data for the new target lateral angle/trajectory/orientation (i.e., for the desired AP angle/trajectory/orientation) is then saved into position memory 224, and preferably selectively stored in first memory unit 225 or second memory unit 226 (and different from where the AP angle was saved). The data for the new target lateral angle/trajectory/orientation may additionally or alternatively be stored in position memory housed externally to the housing of the handheld surgical tool 200—for example, in a separate device like a separate computer, hard drive, etc. This then locks in the second desired angle/trajectory/orientation. As understood from the previous disclosure, during this process the system is only concerned with, and correspondingly measuring, relative movement in a Y-Z plane (e.g., the lateral plane). The system disregards, and does not measure, relative movement in the X-axis. This allows for, for example, the pitch to be selected and locked-in without regard to other angles or orientations, such as yaw.

It is noted that the steps for setting the desired AP and lateral trajectory occur in the first mode of operation (i.e., where at least one positional measurement is disregarded and not measured). And, in order to avoid oversensitivity in the above-described steps, tolerance criteria defining an individual level of tolerance for each angle/trajectory/orientation may be set. Examples for tolerance angle may be a maximum of two degrees.

Figure 5:
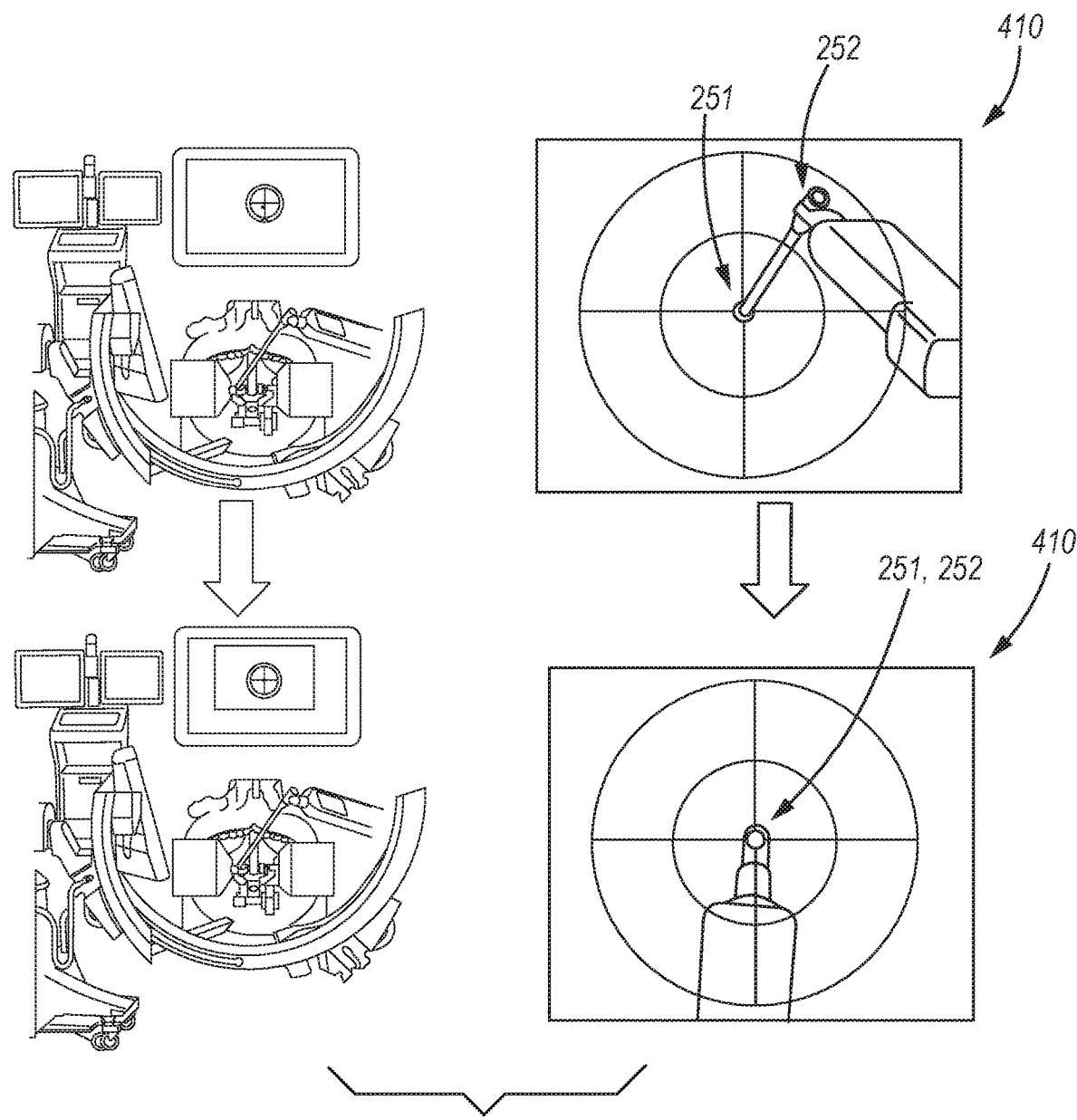
FIG. 5 illustrates components of a surgical navigation system during a second operating step, according to embodiments of the invention.

From the locked-in 2D AP and lateral target angles/trajectory/orientation, a desired 3D trajectory/orientation is established in the system as the target 3D trajectory/orientation, and display 410 is used to orient the shaft 250 of the handheld surgical tool 200 into alignment with the target 3D trajectory/orientation. At this point, the second mode of operation has begun, and the system now monitors movement of the handheld surgical tool in three dimension. Preferably, the distal end of the shaft 250 is placed in real space at the starting point 256. The starting point preferably remains registered on the GUI as the origin point (e.g., X=0, Y=0, Z=0) in the virtual space. Also, a proximal end 252 of the shaft remains registered as a point in the virtual space relative to the starting point in the virtual space, so that the orientation of the shaft in real space relative to the starting point in real space, and relative to the target 3D trajectory/orientation about the starting point (in both AP and lateral planes), is determinable and representable by the system in the virtual space. Then, the handheld surgical tool 200 can be and is moved in real space to angulate the shaft 250 about the starting point in real space until the GUI indicates that the orientation of the shaft in real space relative to the starting point is aligned with the target 3D trajectory/orientation. For example, as the handheld surgical tool 200 is moved, a position of an indicator on the GUI (e.g., a green dot representing a proximal end of the shaft) is shown relative to a position of a target point (e.g., the center of a cross-hairs), and when the positions are aligned, the system has determined that the shaft 250 is oriented in real space, relative to the starting point, in alignment with the target trajectory, and the GUI alerts the user to the alignment (e.g., by changing the GUI color to predominantly green). The display is similar to that as shown in FIGS. 3 and 5.

Preferably, when the positions are aligned, the handheld surgical tool 200 is maintained in real space in the aligned position, and the site is prepared (e.g., the surgeon places the guidewire or drills the pilot hole). At any time during the procedure, X-ray imaging can be used to check the accuracy of the chosen 3D trajectory/orientation.

Although the above steps make reference to X-ray images and the use of AP and lateral planes for the determination of a desired overall trajectory, the invention is not so limited. Rather, any suitable imaging technology and any two non-parallel planes may implemented according to the above-described steps in order to arrive at a desired 3D trajectory/orientation.

According to a modification of the above steps, one alternative embodiment includes adjusting the orientation of the imaging device 500 to a view (e.g., an AP view) such that images taken will show the end-plates of the level to be instrumented. A desired angle/trajectory/orientation (e.g., an AP angle/trajectory/orientation) is established using the handheld surgical tool 200 in combination with continuous imaging or multiple single images (e.g., using surgeon expertise relying on imaging and anatomy landmarks). Preferably, the distal end of the shaft 250 is placed in real space at the starting point 256. Similar to the above embodiments, the starting point is preferably registered on the GUI as a point in the virtual space of the system (e.g., preferably, X=0, Y=0, Z=0; that is, the starting point is preferably set as the origin point in the virtual space). A proximal end 252 of the shaft 250 is registered as a point in the virtual space relative to the starting point in the virtual space, so that the orientation of the shaft in real space relative to the starting point in real space is determinable and representable by the system in the virtual space. Then, the handheld surgical tool 200 can be and is moved in real space to angulate the shaft about the starting point in real space during continuous imaging and/or the taking of multiple single images until the surgeon determines, referencing anatomy shown on the AP X-ray image, that the AP angle/trajectory/orientation at which the shaft is oriented in real space is appropriate. Then, the surgeon confirms this desired AP angle/trajectory/orientation (e.g., by pressing set key 240).

The orientation of the imaging device 500 is then adjusted to a different view (e.g., lateral view) such that images taken will show the end-plates of the level to be instrumented. A desired angle/trajectory/orientation (e.g., a lateral angle/trajectory/orientation) is established using the handheld surgical tool 200 in combination with continuous imaging or multiple single images (e.g., using surgeon expertise relying on imaging and anatomy landmarks). Preferably, the distal end of the shaft 250 is placed in real space at the starting point 256. Similar to the above embodiments, the starting point is preferably registered on the GUI as a point in the virtual space of the system (e.g., preferably, X=0, Y=0, Z=0; that is, the starting point is preferably set as the origin point in the virtual space). A proximal end 252 of the shaft 250 is registered as a point in the virtual space relative to the starting point in the virtual space, so that the orientation of the shaft in real space relative to the starting point in real space is determinable and representable by the system in the virtual space. Then, the handheld surgical tool 200 can be and is moved in real space to angulate the shaft about the starting point in real space during continuous imaging and/or the taking of multiple single images until the surgeon determines, referencing anatomy shown on the lateral X-ray image, that the lateral angle/trajectory/orientation at which the shaft is oriented in real space is appropriate. Then, the surgeon confirms this desired lateral angle/trajectory/orientation (e.g., by pressing set key 240).

If desired, the surgeon can use the GUI during this process to maintain alignment with the desired AP angle/trajectory/orientation (e.g., confirmed in the previous step). However, this is not required. For example, the GUI indicates that the orientation of the shaft 250 in real space, relative to the starting point, is aligned with the desired AP angle. The GUI alerts the user to the alignment (e.g., by changing the GUI color to predominantly green). If the shaft 250 is then moved from this aligned position, a position of an indicator on the GUI (e.g., a green dot representing a proximal end of the shaft) is shown relative to a position of a target point (e.g., the center of a cross-hairs), and when the positions are aligned again, the system has determined that the shaft 250 is oriented in real space, relative to the starting point, in alignment with the desired AP angle/trajectory/orientation, and the GUI indicates that the orientation of the shaft in real space is aligned with the desired AP angle/trajectory/orientation. (For example, the GUI alerts the user to the alignment (e.g., by changing the GUI color to predominantly green)).

Once the desired 3D trajectory (e.g., from the desired 2D AP angle/trajectory/orientation and the desired 2D lateral angle/trajectory/orientation) is established in the system as the target 3D trajectory/orientation, the display 410 is used to orient the shaft of the handheld surgical device 200 into alignment with the target 3D trajectory/orientation. Preferably, the distal end of the shaft is placed in real space at the starting point. The starting point preferably remains registered on the GUI as the origin point in the virtual space. Also, preferably, a proximal end of the shaft remains registered as a point in the virtual space relative to the starting point in the virtual space, so that the orientation of the shaft in real space relative to the starting point in real space, and relative to the target 3D trajectory/orientation about the starting point (in both the AP and lateral planes), is determinable and representable by the system in the virtual space. Then, preferably, the tool 200 can be and is moved in real space to angulate the shaft 250 about the starting point in real space until the GUI indicates that the orientation of the shaft in real space relative to the starting point is aligned with the target 3D trajectory/orientation. For example, as the shaft 250 is moved, a position of an indicator on the GUI (e.g., a green dot representing a proximal end of the shaft) is shown relative to a position of a target point (e.g., the center of a cross-hairs), and when the positions are aligned, the system has determined that the shaft is oriented in real space, relative to the starting point, in alignment with the target 3D trajectory/orientation, and the GUI alerts the user to the alignment (e.g., by changing the GUI color to predominantly green).

Preferably, when the positions are aligned, the handheld surgical tool 200 is maintained in real space in the aligned position, and the site is prepared (e.g., the surgeon places the guidewire or drills the pilot hole). At any time during the procedure, X-ray imaging can be used to check the accuracy of the chosen 3D trajectory/orientation.

According to a still further embodiment, initial default angle/trajectory/orientation values are based upon direct targeting. According to this embodiment, the initial 3D trajectory/orientation can be determined by attaching hardware (e.g., fixation pins) to the target anatomy and then determining the trajectory/orientation at which the hardware is attached. For example, the system can capture the digital trajectory/orientation of a manually placed instrument or implant. According to traditional surgical methods when targeting for implant delivery, it is not uncommon to provisionally place a guidewire, temporary fixation pin, drill bit or the like and take a radiograph to assess the positioning of the provisional placement in relation to known landmarks. In a totally manual environment, the surgeon would need to make an analog adjustment, such as, for example, the final implant placement should be oriented a few degrees more lateral and a few degrees upward. This process is arbitrary, error laden, requires a high level of spatial orientation awareness, and can result in misjudgments and improperly placed hardware.

According to this embodiment, the surgical navigation system 100 can improve upon this process. The shaft 250 of the tool 200 can be placed over a provisionally directed guidewire, fixation pin, or the like, and the system can capture the digital orientation in real time, allowing the surgeon to more accurately adjust the final placement. According to an illustrative example, a temporary fixation element (e.g., pin is attached to the target anatomy). Shaft 250 is then attach (or placed against) this fixation element. Once aligned, set key 240 is pressed, which registers the 3D trajectory/orientation of shaft 250. Thereafter the shaft can be removed. Imaging device 500 then takes a first image (e.g., an AP planar image) which depicts the patients anatomy and the fixation element. Similar to the process described above, the registered trajectory/orientation from the initial alignment of the device provides an indication line in the plane for this registered trajectory/orientation. Using left and right control keys 242, 244, an AP target trajectory/orientation can be modified, until a desired trajectory/orientation is obtained, which can then be locked-in using the set key 240. These steps are subsequently carried out in the lateral plane in order to obtain a lateral target trajectory/orientation. A new target 3D trajectory/orientation is determined based on the AP and lateral, locked-in trajectories/orientations. The fixation element may then be removed. Finally, the shaft 250 of tool 200 is placed at the surgical site, and display 410 may display a bullseye type display (like that shown in FIGS. 3 and 5) to guide proper alignment of shaft 250.

According to another embodiment, the handheld surgical tool 200 is used as previously described, but also replaces alignment module 300. For example, each time an image is imported into the user interface module 400, the handheld surgical tool 200 is positioned relative to the imaging device 500 (e.g., placed on a surface of, or attached to a feature of the C-arm), in the same position each time, to establish a repeatable alignment that is consistent throughout the surgery.

Comparisons of certain of the above-described embodiments will now be made, and are solely for the purpose of providing a better understanding aspects of the present invention. These comparisons are not meant to limit any of the embodiments, nor are they meant limit the scope of the invention as a whole.

As described above, at least one embodiment does not require the implementation of alignment module 300. In this embodiment, the quaternion coming from the sensor(s) 261 in handheld surgical tool 200 are converted (e.g., by processor 220 or by the computer of user interface module 400) into two different 2D orientations in two different intersecting planes (e.g., yaw and pitch, an AP 2D vector and a lateral 2D vector, etc.), and indicates the orientation of the shaft in three-dimensional space. In other embodiments, alignment module 300 is implemented. When implemented, the quaternion coming from the sensors 261 in in handheld surgical tool 200 are not pre-processed (e.g., not first converted to yaw-pitch-roll (i.e., Euler angles), 2D vectors, etc.) and the system takes the quaternions as direct inputs. Additionally, implementing the alignment module 300 into the system allows and enables the system to determine the orientation of the imaging device 500 (e.g., C-arm) in relation to the orientation of handheld surgical tool 200. Therefore, it is not required by the system that imaging device 500 be aligned in any specific orientation.

The processing may also be different between these two embodiments. For example, when no alignment module is implemented, the quaternion coming from the sensor(s) 261 in handheld surgical tool 200 are converted into two different 2D orientations in two different intersecting planes (e.g., yaw and pitch, an AP 2D vector and a lateral 2D vector, etc.). An image in a first plane (e.g., an AP X-ray image) of the two different planes is taken of the relevant interior anatomy and the surgeon positions the shaft 250 in relation to landmarks seen on the AP X-ray image and presses the set key 240 when the shaft 250 is aligned in the AP plane with a trajectory/orientation the surgeon decides is appropriate. Preferably, when the left key is pressed, the AP angle/trajectory/orientation is recorded and saved. This freezes the AP 2D angle/trajectory/orientation (e.g., yaw). An image in a second plane (e.g., a lateral X-ray image) of the two different planes is taken of the relevant anatomy, and the set key 240, when activated (e.g., pressed), additionally freezes the lateral 2D angle/trajectory/orientation so as to freeze both the AP and lateral 2D angles/trajectories/orientations (e.g., a yaw-pitch pair). It is assumed that the lateral plane of the patient is substantially orthogonal to the AP plane of the patient. As an example, a yaw-pitch pair defines the lateral angle (e.g., the angle seen from a perfectly lateral view, parallel to the sagittal plane, which is orthogonal to the axial and coronal planes). That is, the angle (e.g., the trajectory on the X-ray image) seen from the lateral view is affected by the yaw angle. The anatomical trajectory is defined by two angles because the pitch is the angle between the shaft and the gravity plane, but the lateral angle is the projection of the pitch onto the sagittal plane (e.g., the lateral X-ray image). Stated alternatively, the yaw (e.g., the trajectory chosen in the AP view) affects how the trajectory is seen in the lateral view. That is, the same trajectory defined in the lateral view could be defined by an infinite series of yaw-pitch pairs, where the pitch would depend on the previously chosen yaw.)

Therefore, one of two possible approaches is then taken: positioning the shaft in the lateral plane either (1) while maintaining AP alignment or (2) without maintaining AP alignment.

In the first approach, while maintaining alignment of the shaft 250 of handheld surgical tool 200 in the AP plane with the AP 2D angle/trajectory/orientation previously recorded, the surgeon positions the shaft in relation to landmarks seen on the lateral X-ray image and presses the set key 240 when the shaft 250 is aligned in the lateral plane with a lateral 2D trajectory/orientation the surgeon decides is appropriate (e.g., desired). When the set key 240 is pressed, the AP and lateral 2D angles/trajectories/orientations are recorded and saved. Because alignment with the previously recorded AP angle/trajectory/orientation has been maintained, only 1 AP angle/trajectory/orientation (e.g., yaw) has been recorded and 1 lateral angle/trajectory/orientation (e.g., pitch) has been recorded and the AP—lateral 2D orientation pair (e.g., a yaw-pitch pair) corresponds to the desired three-dimensional trajectory without the need for additional calculations.

In the second approach, without maintaining alignment of the shaft 250 of handheld surgical tool 200 in the AP plane with the AP 2D angle/trajectory/orientation previously recorded, the surgeon positions the shaft 250 in relation to landmarks seen on the lateral X-ray image and presses the set key 240 when the shaft is aligned in the lateral plane with a lateral 2D trajectory/orientation the surgeon decides is appropriate (e.g., desired). Preferably, when the set key 240 is pressed, the AP and lateral 2D angles/trajectories/orientations are recorded and saved. Because alignment with the previously recorded AP angle/trajectory/orientation has not been maintained, the system then calculates, from the recorded AP and lateral 2D angles/trajectories/orientations, a the desired three-dimensional trajectory/orientation. The resulting quaternion corresponds to the orientation with which the shaft 250 of handheld surgical tool 200 must be aligned for use to place a surgical item (e.g., K-wire and/or screw) according to the desired three-dimensional trajectory/orientation. For example, from an AP 2D vector and a lateral 2D vector, the system calculates the desired 3D vector with which the shaft 250 of handheld surgical tool 200 must be aligned.

When the alignment module 300 is implemented, the system does not require the imaging device 500 to be aligned in a specific orientation. An image in a first plane (e.g., the AP plane) is taken when the surgeon positions the shaft 250 of handheld surgical tool 200 in relation to landmarks seen on the AP X-ray image and presses the set key 240 when the shaft is aligned with a trajectory/orientation the surgeon decides is appropriate (e.g., desired) or when the surgeon virtually modifies the desired angle/trajectory/orientation. Preferably, when the set key 240 is pressed, the quaternion coming from the sensor(s) 261 in handheld surgical tool 200 and the quaternion coming from the sensor in alignment module 300 (e.g., pair quatH-quatF or triplet quatH-quatF-correction) are recorded and saved (e.g., as a first quaternion pair or triplet). An image in a second plane (e.g., the lateral plane) is taken when the surgeon positions the shaft 250 of handheld surgical tool 200 in relation to landmarks seen on the lateral X-ray image and presses the set key 240 when the shaft is aligned with a trajectory/orientation the surgeon decides is appropriate (e.g., desired) or when the surgeon virtually modifies the desired angle/trajectory/orientation. Preferably, when the set key 240 is pressed, the quaternion coming from the sensor(s) 261 in handheld surgical tool 200 and the quaternion coming from the sensor in alignment module 300 (e.g., pair quatH-quatF or triplet quatH-quatF-correction) are recorded and saved (e.g., as a second quaternion pair or triplet). The system then determines, from the first and second quaternion pairs (or triplets), a single desired quaternion that corresponds to the desired three-dimensional trajectory/orientation. That is, preferably, the resulting desired quaternion corresponds to the orientation with which the shaft of Module H must be aligned for use to place a surgical item (e.g., K-wire and/or screw) according to the desired three-dimensional trajectory.

As mentioned above, the information collected for each view/plane includes QuatH-QuatF where: QuatH is the quaternion coming from the handheld tool 200 and QuatF is the quaternion coming from the Alignment Module 300. The image data may also be paired with the quaternion(s). Using, for example, a Hamilton product, the quaternion(s) are converted to a 3-dimensional vector. The vector associated with the handheld tool 200 is projected onto the plane represented by the vector associated with the Alignment Module 300. The resulting 2-dimensional vector represents the mathematical/geometrical version of what is seen in the X-ray image. The X-ray image is preferably then processed to detect the direction of the shaft of the instrument and its center of rotation (COR). Preferably, the COR represents the point about which the shaft is rotating in this plane when a change of trajectory is applied in real space. Preferably, applying a correction to the X-ray image (about the COR) relates to a direct correction to the 2-dimensional vector. Preferably, using a fusion algorithm (e.g., least square regression), the 2-dimensional trajectories/orientations can be converted into a unique 3-dimensional trajectory/orientation.

The above-described systems and methods are meant to be illustrative, and alternative computer-aided surgical navigation systems and methods are within the scope of this disclosure. For example, the systems and methods may be carried out with different imaging technology, do not specifically require imaging in the AP and lateral plane (or any two orthogonal planes) and are not limited to spinal procedures.

The invention claimed is:

1. A surgical navigation system comprising:
a surgical tool comprising:
an instrument shaft having a distal end opposite to and distal from a proximal end of the instrument shaft;
at least one sensor unit configured to produce positional information representing a three-dimensional orientation of the instrument shaft in a real space of the surgical navigation system; and
one or more processors configured to determine a three-dimensional orientation of the instrument shaft in a virtual space of the surgical navigation system, the determination comprising:
identifying an origin point of the instrument shaft in the virtual space based on a positional information describing a position of the distal end of the instrument shaft relative to a surgical location;
determining a point in the virtual space corresponding to the proximal end of the instrument shaft based on positional information describing a position of the proximal end in the real space;
determining the three-dimensional orientation of the instrument shaft in the virtual space based on the origin point of the instrument shaft in the virtual space and the point in the virtual space corresponding to the proximal end of the instrument shaft;
determining first plane positional information corresponding to an orientation of the instrument shaft in a first plane;
determining a first-plane difference between the orientation of the instrument shaft in the first plane and a target first plane orientation;
determining second plane positional information corresponding to an orientation of the instrument shaft in a second plane; and
determining a second-plane difference between the orientation of the instrument shaft in the second plane and a target second plane orientation; and
a user interface configured to display:
the three-dimensional orientation of the instrument shaft in the virtual space; and
a target three-dimensional orientation of the instrument shaft in the virtual space, the target three-dimensional orientation representing a default orientation for operating the surgical tool at the surgical location, wherein the displayed target three-dimensional orientation further comprises the target first plane orientation and the target second plane orientation; and
an alignment between the three-dimensional orientation of the instrument shaft in the virtual space and the target first plane orientation and the target second plane orientation, wherein the user interface dynamically updates the displayed difference in response to angular movement of the instrument shaft about a starting point of the instrument shaft in the real space and dynamically updates an endpoint of a trajectory of the instrument shaft in the virtual space;
an indicator line in the virtual space, wherein the user interface is configured to receive an input to change an indicator line trajectory of the indicator line by rotating the indicator line about the starting point; and
an imaging device configured to capture a lateral X-ray image of the surgical location in response to the three-dimensional orientation of the instrument shaft in the virtual space aligning with the target three-dimensional orientation of the instrument shaft in the virtual space, wherein the lateral X-ray image captures anatomy at the surgical location and the instrument shaft, wherein the one or more processors are further configured to perform:
utilizing three-dimensional positional information corresponding to a three-dimensional orientation of the imaging device when taking a first X-ray image to determine an orientation of the instrument shaft in the first plane passing through the surgical location; and
utilizing three-dimensional positional information corresponding to a three-dimensional orientation of the imaging device when taking a second X-ray image to determine an orientation of the instrument shaft in the second plane passing through the surgical location.

2. The surgical navigation system of claim 1, wherein the one or more processors are further configured to:
determine the first-plane difference between the first plane orientation of the instrument shaft in the first plane and the target first plane orientation of the instrument shaft in the first plane, wherein the first-plane difference is determined by changing an orientation of the instrument shaft in a first plane of the virtual space.

3. The surgical navigation system of claim 1, wherein the one or more processors are further configured to:
determine the target three-dimensional orientation of the instrument shaft based on the target first plane orientation and the target second plane orientation; and
monitor the alignment of the instrument shaft with the target three-dimensional orientation based on changes in the first-plane difference and the second-plane difference.

4. The surgical navigation system of claim 1, wherein the one or more processors determine the second-plane difference by a changing an orientation of the instrument shaft in a second plane of the virtual space from a first virtual second-plane orientation corresponding to the orientation of the instrument shaft in the second plane to a second virtual second-plane orientation corresponding to the target second-plane orientation.

5. The surgical navigation system of claim 1, wherein the one or more processors determine the target three-dimensional orientation of the instrument shaft based on second-plane positional information corresponding to the orientation of the instrument shaft in the second plane of the virtual space.

6. The surgical navigation system of claim 1, wherein the one or more processors determine the first-plane difference by changing the orientation of the instrument shaft in the first plane to the target first-plane orientation.

7. The surgical navigation system of claim 1, wherein the one or more processors determine the target three-dimensional orientation of the instrument shaft based on first-plane positional information corresponding to the target first-plane orientation.

8. The surgical navigation system of claim 1, wherein the one or more processors determine the second-plane difference by changing the orientation of the instrument shaft in the second plane to the target second-plane orientation.

9. The surgical navigation system of claim 1, wherein the one or more processors determine the target three-dimensional orientation of the instrument shaft based on second-plane positional information corresponding to the target second-plane orientation.

10. The surgical navigation system of claim 1, further comprising:
an alignment module comprising:
at least one sensor unit configured to produce three-dimensional positional information corresponding to a three-dimensional orientation of the imaging device; and
a transmitter configured to transmit the three-dimensional positional information of the imaging device to the one or more processors.

11. The surgical navigation system of claim 1, wherein the user interface is further configured to update the indicator line trajectory in the virtual space.

12. A method for positioning a surgical tool, the method comprising:
identifying, by one or more processors, an origin point of an instrument shaft of the surgical tool in a virtual space of a surgical navigation system based on a positional information describing a position of a distal end of the instrument shaft relative to a surgical location;
determining a point in the virtual space corresponding to the proximal end of the instrument shaft based on positional information describing a position of a proximal end in the real space;
determining a three-dimensional orientation of the instrument shaft in the virtual space based on the origin point of the instrument shaft in the virtual space and the point in the virtual space corresponding to the proximal end of the instrument shaft in the virtual space;
determining first plane positional information corresponding to an orientation of the instrument shaft in a first plane;
determining a first-plane difference between the orientation of the instrument shaft in the first plane and a target first plane orientation;
determining second plane positional information corresponding to an orientation of the instrument shaft in a second plane;
determining a second-plane difference between the orientation of the instrument shaft in the second plane and a target second plane orientation; and
displaying, by a user interface:
the three-dimensional orientation of the instrument shaft in the virtual space; and
a target three-dimensional orientation of the instrument shaft in the virtual space, the target three-dimensional orientation representing a default orientation for operating the surgical tool at the surgical location, wherein the displayed target orientation further comprises the target first plane orientation and the target second plane orientation;
an alignment between the three-dimensional orientation of the instrument shaft in the virtual space and the target first plane orientation and the target second plane orientation, wherein the user interface dynamically updates the displayed difference in response to angular movement of the instrument shaft about a starting point of the instrument shaft in the real space and dynamically updates an endpoint of a trajectory of the instrument shaft in the virtual space; and
an indicator line in the virtual space, wherein the user interface is configured to receive an input to change an indicator line trajectory of the indicator line by rotating the indicator line about the starting point;
capturing, by an imaging device, a lateral X-ray image of the surgical location in response to the three-dimensional orientation of the instrument shaft in the virtual space aligning with the target three-dimensional orientation of the instrument shaft in the virtual space, wherein the lateral X-ray image captures anatomy at the surgical location and the instrument shaft;
utilizing three-dimensional positional information corresponding to a three-dimensional orientation of the imaging device when taking a first X-ray image to determine an orientation of the instrument shaft in the first plane passing through the surgical location; and
utilizing three-dimensional positional information corresponding to a three-dimensional orientation of the imaging device when taking a second X-ray image to determine an orientation of the instrument shaft in the second plane passing through the surgical location.

13. The method of claim 12, further comprising:
determining the first-plane difference between the first plane orientation of the instrument shaft in the first plane and the target first plane orientation of the instrument shaft in the first plane, wherein the first-plane difference is determined by changing an orientation of the instrument shaft in a first plane of the virtual space.

14. The method of claim 12, further comprising:
determining the target three-dimensional orientation of the instrument shaft the target first plane orientation and the target second plane orientation; and
monitor the alignment of the instrument shaft with the target three-dimensional orientation based on changes in the first-plane difference and the second-plane difference.

15. The method of claim 12, wherein determining the second-plane difference further comprises:
changing an orientation of the instrument shaft in a second plane of the virtual space from a first virtual second-plane orientation corresponding to the orientation of the instrument shaft to a second virtual second-plane orientation corresponding to the target second-plane orientation.

16. The method of claim 12, wherein the target three-dimensional orientation of the instrument shaft is determined based on second plane positional information corresponding to the orientation of the instrument shaft in the second plane of the virtual space.

17. The method of claim 12, wherein determining the first-plane difference further comprises:
changing the orientation of the instrument shaft in the first plane to the target first-plane orientation.

18. The method of claim 12, wherein the target three-dimensional orientation is determined based on first plane positional information corresponding to the target first-plane orientation.

19. The method of claim 12, wherein determining the second-plane difference further comprises:
changing the orientation of the instrument shaft in the second plane to a target second-plane orientation.

20. The method of claim 12, wherein the target three-dimensional orientation is determined based on second plane positional information corresponding to the target second-plane orientation.

21. The method of claim 12, wherein the user interface is further configured to update the indicator line trajectory in the virtual space.

* * * * *